(12) United States Patent
Stinson

(10) Patent No.: US 7,740,798 B2
(45) Date of Patent: Jun. 22, 2010

(54) ALLOY COMPOSITIONS AND DEVICES INCLUDING THE COMPOSITIONS

(75) Inventor: Jonathan S. Stinson, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 467 days.

(21) Appl. No.: 11/738,672

(22) Filed: Apr. 23, 2007

(65) Prior Publication Data
US 2007/0189917 A1    Aug. 16, 2007

Related U.S. Application Data

(62) Division of application No. 10/690,717, filed on Oct. 22, 2003, now Pat. No. 7,329,383.

(51) Int. Cl.
  C22C 5/02    (2006.01)
  C22C 5/04    (2006.01)
  C22C 5/06    (2006.01)
  C22C 11/00   (2006.01)

(52) U.S. Cl. .......... 420/461; 420/463; 420/462; 420/512; 420/506; 420/563

(58) Field of Classification Search .......... 420/463–465, 420/461, 462, 512, 501–506, 563–575, 35
See application file for complete search history.

(56) References Cited

U.S. PATENT DOCUMENTS

| | | |
|---|---|---|
| 3,174,851 A | 3/1965 | Buehler et al. |
| 3,351,463 A | 11/1967 | Rozner et al. |
| 3,753,700 A | 8/1973 | Harrison et al. |
| 3,970,450 A * | 7/1976 | Liu et al. ............ 420/461 |
| 4,668,290 A | 5/1987 | Wang et al. |
| 4,958,625 A | 9/1990 | Bates et al. |
| 5,090,419 A | 2/1992 | Palestrant |
| 5,209,799 A | 5/1993 | Vigil |
| 5,238,004 A | 8/1993 | Sahatjian et al. |
| 5,336,234 A | 8/1994 | Vigil et al. |
| 5,368,045 A | 11/1994 | Clement et al. |
| 5,800,511 A | 9/1998 | Mayer |
| 5,888,201 A | 3/1999 | Stinson et al. |
| 6,146,404 A | 11/2000 | Kim et al. |
| 6,171,327 B1 | 1/2001 | Daniel et al. |
| 6,342,062 B1 | 1/2002 | Suon et al. |
| 6,508,803 B1 | 1/2003 | Horikawa et al. |
| 2004/0133223 A1 | 7/2004 | Weber |
| 2005/0051243 A1 | 3/2005 | Forbes Jones et al. |
| 2006/0165554 A1 * | 7/2006 | Coupland et al. ........ 420/461 |

FOREIGN PATENT DOCUMENTS

JP        55131157 A  *  10/1980

OTHER PUBLICATIONS

Kiser, "Preventing Weld Corrosion", *Advanced Materials & Processes*, 2002, 32-35.

* cited by examiner

*Primary Examiner*—Roy King
*Assistant Examiner*—Janelle Morillo
(74) *Attorney, Agent, or Firm*—Fish & Richardson P.C.

(57) ABSTRACT

Alloy compositions, including devices and instruments that include the compositions, are disclosed. The compositions have high hardness, strength, corrosion resistance, and biocompatibility. The compositions can be used to manufacture, for example, medical devices and products.

8 Claims, 1 Drawing Sheet

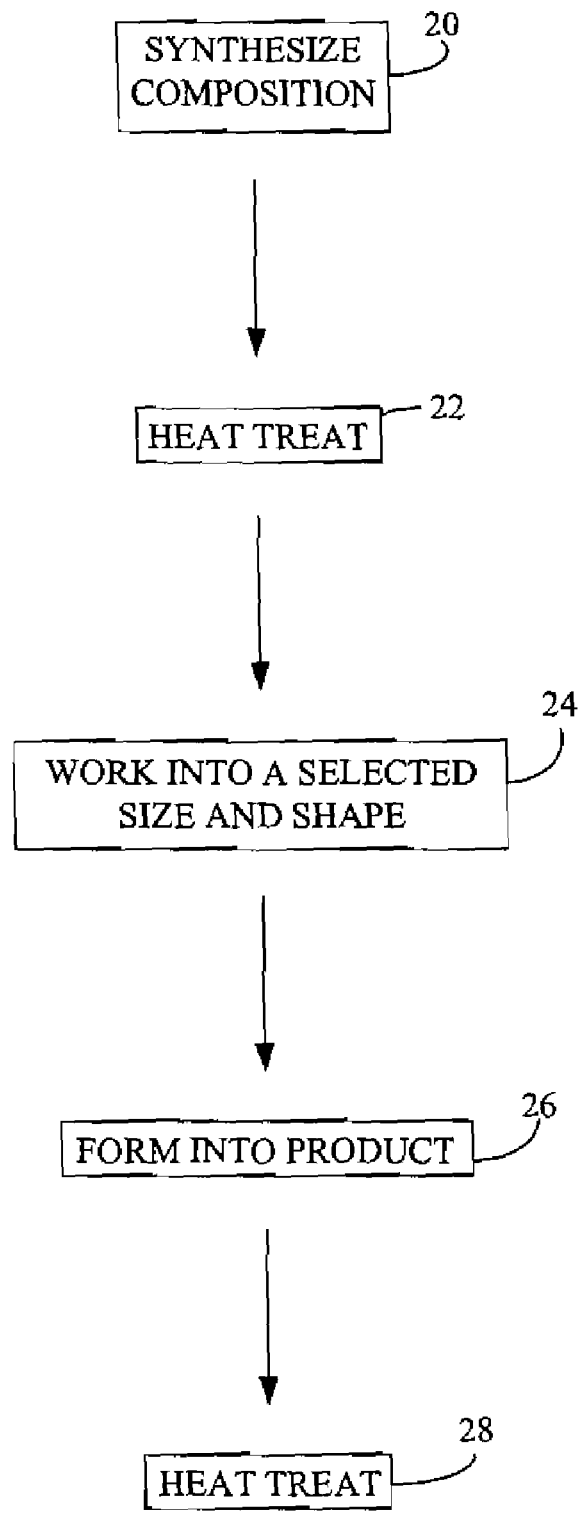
Figure

ALLOY COMPOSITIONS AND DEVICES INCLUDING THE COMPOSITIONS

CROSS-REFERENCE TO RELATED APPLICATIONS

This application is a divisional application of and claims priority to U.S. application Ser. No. 10/690,717, filed on Oct. 22, 2003, now U.S. Pat. No. 7,329,383 the entire contents of which are hereby incorporated by reference.

TECHNICAL FIELD

The invention relates to alloy compositions and devices, such as medical implants, medical instruments, and non-medical industrial and commercial products, including the compositions.

BACKGROUND

Stainless steels are alloys that include iron and other elements such as chromium, nickel, and molybdenum. The alloys can exhibit high hardness, high tensile strength, and high resistance to corrosion.

As a result, stainless steels can be used to manufacture a variety of products. For example, stainless steels can be used to form medical devices (such as stents and orthopedic implants) and medical instruments (such as scalpels). The stainless steels can provide the devices and instruments with the hardness and strength to resist wear and deformation, which can lead to failure. At the same time, the stainless steels can provide good corrosion resistance, for example, when the devices or instruments are exposed to repeated steam autoclave sterilization or to electrolytic conditions in the body that can facilitate corrosion.

SUMMARY

The invention relates to alloy compositions and devices including the compositions.

In one aspect, the invention features a medical device including an alloy having less than about 22 weight percent of chromium, less than about 4 weight percent of molybdenum, greater than about 50 weight percent of platinum, and iron.

Embodiments may include one or more of the following features. The alloy includes from about 3 to about 22 weight percent of chromium. The alloy includes from about 1 to about 4 weight percent of molybdenum. The alloy includes greater than about 55 weight percent of platinum, e.g., greater than about 60, 65, 70, 75, 80, or 90, weight percent of platinum. The alloy further includes nickel, e.g., less than about 6 weight percent of nickel. The alloy further includes copper, manganese, nickel, phosphorus, silicon, nitrogen, sulfur, and carbon. The alloy includes less than about 25 weight percent of iron.

The alloy can have one or more of the following properties. The alloy is substantially fully martensitic, or at least about 50% martensitic, e.g., at least about 70% or 90% martensitic. The alloy has a pitting resistance equivalent of greater than about 26. The alloy has a hardness of greater than about 24 HRC. The alloy has a tensile strength of greater than about an ultimate tensile strength of 140 ksi. The alloy has a density of greater than about 11 g/cc.

Embodiments of the device can have various forms. The device can be adapted to be implanted in a body. The device can be in the form of a fixation device, a prosthesis, a hip stem, a knee tray, or a dental prosthesis. The device can be adapted to be a surgical instrument. The instrument can be in the form of a pair of forceps, a clamp, a needle, a pair of scissors, or a scalpel. The device can be in the form of a balloon catheter including a cutting element having the alloy.

In another aspect, the invention features a medical device including an alloy having a stainless steel and greater than about 50% by weight of one or more first elements selected from platinum, palladium, iridium, rhodium, gold, silver, and/or lead.

Embodiments may include one or more of the following features. The stainless steel is a 300 series stainless steel, such as 316 stainless steel. The alloy includes greater than about 60% by weight of the first element, e.g., greater than about 70% by weight of the first element. The alloy includes chromium and molybdenum. The alloy is at least about 50% martensitic. The first element is platinum. The alloy consists essentially of the stainless steel, one or more first elements, chromium, and molybdenum. The stainless steel is a 300 series stainless steel, the first element is platinum, and the alloy includes less than about 22 weight percent of chromium, and less than about 4 weight percent of molybdenum.

In another aspect, the invention features a medical device including an alloy having a hardness greater than about 24 HRC and a pitting resistance equivalent greater than about 26. The alloy is at least 50% martensitic.

Embodiments may include one or more of the following features. The alloy has an ultimate tensile strength greater than about 140 ksi. The alloy has a density greater than about 11 g/cc. The alloy has a radiopacity greater than 316L stainless steel.

In another aspect, the invention features a composition including less than about 22 weight percent of chromium, less than about 4 weight percent of molybdenum, greater than about 50 weight percent of platinum, and iron.

Embodiments may include one or more of the following features. The composition has from about 3 to about 22 weight percent of chromium. The composition has from about 1 to about 4 weight percent of molybdenum. The composition has greater than about 55 weight percent of platinum. The composition has nickel, e.g., less than about 6 weight percent. The composition further includes copper, manganese, nickel, phosphorus, silicon, nitrogen, sulfur, and carbon. The composition has less than about 25 weight percent of iron. The composition is substantially fully martensitic, e.g., at least about 50%, 70%, or 90% martensitic. The composition has a pitting resistance equivalent of greater than about 26. The composition has a hardness of greater than about 24 HRC and/or an ultimate tensile strength of greater than about 140 ksi. The composition has a density of greater than about 11 g/cc.

Embodiments may have one or more of the following advantages. The alloy compositions can have high hardness (e.g., similar to tool steel) and high corrosion resistance. The compositions can have high radiopacity, and as a result, the compositions can be monitored using X-ray fluoroscopy. In some embodiments, the compositions have a relatively low nickel concentration (e.g., relative to 316L or 304L surgical steel), which can enhance the biocompatibility of the compositions. The alloy compositions can be used to form a variety of products, including medical devices, medical instruments, geological and petroleum drilling equipment, marine (e.g., underwater) equipment, and architectural structures.

As used herein, an "alloy" means a substance composed of two or more metals or of a metal and a nonmetal intimately united, for example, by being fused together and dissolving in each other when molten.

Other aspects, features and advantages of the invention will be apparent from the description of the preferred embodiments and from the claims.

DESCRIPTION OF DRAWING

The FIGURE is a flow chart illustrating a method of manufacturing a product.

DETAILED DESCRIPTION

The invention features alloy compositions and products including the compositions. The compositions have one or more physical and/or mechanical properties, such as radiopacity, hardness, strength, elongation, and resistance to corrosion, that are suitable for medical or non-medical uses. In some embodiments, the compositions are formed by combining (e.g., melting) a stainless steel (such as 316L stainless steel) with one or more elements (such as Pt) capable of enhancing the steel, such as its hardness. As a result, the compositions can have a corrosion resistance and/or biocompatibility similar to that of a stainless steel and the high hardness of tool steel. The compositions can then be formed into products (such as implantable prostheses) that benefit from a combination of such properties.

Referring to Table 1 shown below, the alloys can include, among others, chromium, molybdenum, iron, and an element X:

TABLE 1

Alloy Compositions

| Element | Weight Percent |
| --- | --- |
| Chromium | from about 3 to about 22 |
| Molybdenum | from about 1 to about 5 |
| Element X | greater than about 50 |
| Iron | balance (e.g., between 0 and about 25) |

Element X can include one or more (e.g., two, three, four, five, six or more) of elements having an atomic weight from about 100 to about 239, such as from about 180 to about 210. In embodiments, element X has a crystallographic lattice parameter "a" of greater than or equal to about 2.86, such as greater than or equal to about 3.80. Examples of element X include platinum, iridium, rhodium, hafnium, tantalum, tungsten, gold, palladium, silver, and lead. In addition, the alloys may include one or more of the following elements: carbon, nitrogen, manganese, copper, zinc, silicon, phosphorus, and nickel.

Without wishing to be bound by theory, it is believed that chromium can enhance the corrosion resistance of the alloys, e.g., by increasing the pitting resistance of the alloy. For example, in certain stainless steels, at 12 weight percent or higher, chromium can form a thin oxide layer on the surface of a steel that enhances the resistance of the steel to corrosive attack. The degree of corrosion resistance can be a function of the chromium concentration and the concentrations of other elements in the steel. The alloys can include from about 3 to about 22 weight percent of chromium. The alloys can include greater than or equal to about 3, 4, 5, 6, 7, 8, 9, 10, 11, 12, 13, 14, 15, 16, 17, 18, 19, 20, or 21 weight percent, and/or less than or equal to 22, 21, 20, 19, 18, 17, 16, 15, 14, 13, 12, 11, 10, 9, 8, 7, 6, 5, or 4 weight percent of chromium.

Molybdenum can also be added to the alloys to enhance the resistance of the alloys to corrosion, e.g., pitting and crevice corrosion. In embodiments, the alloys include from about 1 to about 4 weight percent of molybdenum. For example, the alloys can include greater than or equal to about 1, 1.25, 1.5, 1.75, 2, 2.25, 2.5, 2.75, 3, 3.25, 3.5 or 3.75 weight percent, and/or less than or equal to 4, 3.75, 3.5, 3.25, 3, 2.75, 2.5, 2.25, 2, 1.75, 1.5, or 1.25 weight percent of molybdenum.

Element X (e.g., Pt, Ta, Hf, W, Pd, Ir, Rh, Pb, Ag, and Au) is selected from a group of elements capable of enhancing the alloys, e.g., their strength, hardness, and/or radiopacity. Without wishing to be bound by theory, it is believed that element X is capable of solid solution strengthening the alloys by distorting the structural lattice of the alloys such that the lattice strains and the alloys strengthen. For example, the lattice parameter "a" of element X can be larger than the lattice parameter "a" for iron (Fe=2.866). As a result, when element X atom is incorporated into the crystallographic lattice, distortion (strain) results and the material is strengthen. In some embodiments, element X has a density equal to or greater than that of iron (7.87 g/cc). The high density of element X can increase the radiopacity (i.e., visibility to X-rays) of the alloy compositions, e.g., relative to conventional commercially available iron-based stainless steel alloys (such as 316L, 304L and 410), which then allows certain products formed from the alloys (such as medical implants) to be monitored by X-rays. The high concentration of element X can also increase the density of the alloys. In some embodiments, the alloys have a density greater than about 11 g/cc, e.g., greater than about 11.5, 12.0, 12.5, or 13.0 g/cc. The high density of the alloys can allow them to be, for example, effective anchors or ballasts.

The alloy can include a total of from about 50 to about 90 weight percent of one or more element X. The alloys can include greater than or equal to about 50, 55, 60, 65, 70, 75, 80, or 85 weight percent, and/or less than or equal to about 90, 85, 80, 75, 70, 65, 60, or 55 weight percent of element X.

In certain embodiments, the alloys contain nickel. The alloys can have less than about 5.5 percent by weight of nickel. For example, the alloy can have less than or equal to 5.5, 5, 4.5, 4, 3.5, 3, 2.5, 2, or 1.5 percent by weight of nickel; and/or greater than or equal to 1, 1.5, 2, 2.5, 3, 3.5, 4, or 4.5 percent by weight of nickel. In some embodiments, the alloys are substantially free of nickel, i.e., having less than or equal to 1% by weight of nickel (e.g., less than or equal to 0.05 or 0.03% by weight). It is believed that nickel can cause an allergic and/or cytotoxic effect in certain subjects. Therefore, by reducing the amount of nickel in the alloy, the occurrence of the effect(s) can be reduced (e.g., minimized or eliminated).

The alloys can further include microalloyed elements or residual amounts of impurities elements. For example, the alloys may include phosphorus (e.g., 0.025 wt % maximum), silicon (e.g. 0.75 wt % maximum), sulfur (e.g., 0.010 wt % maximum), niobium (e.g., about 0.013 wt %), vanadium (e.g., about 0.07 wt %), titanium (e.g., 0.002 wt %), copper (e.g., about 0.2 wt %), selenium (e.g., about 0.2 wt %) and/or aluminum (e.g., about 0.009 wt %). Other microalloyed and residual elements are possible, which can be a function of the source of the materials.

Iron makes up the balance of the alloys, e.g., after accounting for the other elements in the alloys described above. In certain embodiments, the alloys include greater than 0 and less than about 25 weight percent of iron. For example, the alloys can include less than about 25, 23, 21, 19, 17, 15, 13, 11, 9, 7, 5, or 3 weight percent of iron.

The alloys can be synthesized by intimately combining the components of the alloys. In some embodiments, samples of an alloy composition are made by melting charges of the components of the alloy. For example, at least 50 weight percent (e.g., >60 weight percent or >70 weight percent) of platinum can be melted with 316L stainless steel, and additional chromium metal and/or additional molybdenum metal (for corrosion resistance) to form a targeted alloy composition. Alternatively, the targeted alloy composition can be formed by melting elemental powders in the appropriate concentrations. Melting can be performed using vacuum induction melting (VIM), vacuum arc remelting (VAR), electron beam melting (EBM), plasma melting, vacuum or inert gas plasma deposition, hot isostatic pressing, and/or cold pressing and sintering. The samples can be in the form of an ingot, a compact, or a deposit.

The alloy samples are then processed (e.g., by heat treatment) to yield materials with selected structure and properties. In preferred embodiments, the alloys have a microstructure that is predominantly (greater than 50%) martensitic, i.e., the alloys are formed predominantly of the martensite phase. It is believed that the martensitic microstructure provides the alloys with their high tensile strength and hardness. In some cases, the alloys can be equal to or greater than about 50%, 55%, 60%, 65%, 70%, 75%, 80%, 85%, 90%, or 95% martensitic. Preferably, the alloys are substantially fully martensitic.

In some embodiments, the alloys have high corrosion resistance. The corrosion resistance properties can be characterized as a pitting resistance equivalent (PRE), which can be calculated as $$PRE = \% Cr + 3.3(\%)Mo + 30N$$

where Cr, Mo, and N, respectively, are the weight percent concentrations of chromium, molybdenum, and nitrogen in the alloys. More information about PREs can be found in S. D. Kiser, Preventing Weld Corrosion, *Advanced Materials & Processes*, March 2002, pp. 32-35. In preferred embodiments, the alloys have a pitting resistance equivalent equal to or greater than about 26.

The alloys can also have high hardness and/or high strength. In some embodiments, the alloys have a Rockwell hardness greater than about 24 HRC, e.g., greater than about 30, 35, 40, 45, or 55 HRC. The alloys can have an ultimate tensile strength (UTS) of greater than about 140 ksi, e.g., greater than about 180, 200, or 220.

Referring to the FIGURE, a method of manufacturing a product from the alloys is shown. First, samples of the alloys are synthesized (e.g., by melting the components of the alloys) (step 20), and then, the samples are heat treated (step 22). The heat treatment homogenizes the samples by reducing (e.g., removing) any heterogeneity in the samples from segregation of the elements caused by melting and solidification. The heat treatment also produces the martensitic structure in the alloy. In some embodiments, the samples are heat treated at about 1300° C. for about six hours and slow cooled.

The heat treated samples are then formed into a size and shape suitable for further processing (step 24). For example, the samples can be hot worked to form a billet, a bar, a plate, a strip, a foil, or a tubing. Alternatively or in addition the samples can be cold worked with intermediate annealing and/or heat tempering steps to achieve the desired shape and size.

The samples can then be formed into a product using manufacturing techniques (step 26). For example, the samples can be forged and/or machined to form a product. In some cases, the product can be finished with a final heat treatment that produces a tempered martensite microstructure with a balance of strength, hardness, and ductility tailored for the intended application (step 28).

The combination of high hardness, high strength, and high corrosion resistance allows the alloys to be formed into a variety of products. For example, the alloys can be used to form medical products. The alloys can be used to form medical instruments, such as forceps, clamps, needles, scissors, and scalpels, that benefit from having high strength and/or high hardness. The alloys can also be used to manufacture cutting elements, such as those carried by a medical balloon catheter described in U.S. Ser. No. 10/335,604, filed Jan. 2, 2003, and U.S. Pat. No. 5,209,799, and U.S. Pat. No. 5,336,234. The hardness and strength of the alloys can reduce edge rounding (which can decrease sharpness) and deformation of the product shape. Also, in some cases, the relatively high corrosion resistance of the alloys allows the instruments to be exposed to repeated steam autoclave sterilization cycles. As a result, the instruments can be reused more, and the cost of replacement is reduced.

The alloys can be used to form medical devices that benefit from having high strength to resist overloading and fracture, high corrosion resistance, and/or biocompatibility (e.g., capable of being implanted in a body for long periods (such as greater than ten years)). Suitable examples of devices include internal and external fixation devices, hip stems, knee trays, and dental prostheses.

The alloys also can be used to manufacture other endoprostheses. For example, the alloys can be used in filters such as removable thrombus filters described in Kim et al., U.S. Pat. No. 6,146,404, which is hereby incorporated by reference; in intravascular filters such as those described in Daniel et al., U.S. Pat. No. 6,171,327, which is hereby incorporated by reference; and vena cava filters such as those described in Soon et al., U.S. Pat. No. 6,342,062, which is hereby incorporated by reference.

The alloys can also be used in guidewires such as a Meier Steerable Guide Wire (for AAA stent procedure) and an ASAP Automated Biopsy System described in U.S. Pat. Nos. 4,958,625, 5,368,045, and 5,090,419, which are hereby incorporated by reference herein.

The alloys can be used for non-medical purposes. For example, the alloys can be used to form products that benefit from having high strength and high corrosion resistance to withstand severe loading and environmental conditions. The alloys can be used as components in geological and/or petroleum drilling, marine equipment or structures that are exposed to harsh, corrosive conditions, and structural components. The high density of the alloys can make them useful as marine anchors and ballast bars, balance beam components, ordnance projectiles, and other applications in which high density, strength, hardness, and corrosion resistance are desired. The high hardness and corrosion resistance of the alloys are beneficial for forming cutting edges, such as for razor blades, knife blades, and scissors.

The following examples are illustrative and not intended to be limiting.

EXAMPLES

The following examples describe the characterization of three alloy compositions. The compositions were synthesized by combining 316L stainless steel (available from Carpenter Biodur) with 50, 60, or 70 percent by weight of platinum metal. In these examples, additional chromium metal and molybdenum metal were added to obtain a nominal Cr Concentration of 17.83 weight percent, and a nominal Mo concentration of 2.65 weight percent (to provide pitting corrosion resistance and self-passivation). As shown below, as the platinum concentration increases, the iron and nickel concentrations decrease.

TABLE 2

|  | 50% by weight Pt | 60% by weight Pt | 70% by weight Pt |
|---|---|---|---|
| Cr | 17.454 | 18.062 | 17.880 |
| Ni | 5.5588 | 3.5964 | 1.7184 |
| Mo | 2.1053 | 2.0096 | 2.0528 |
| Mn | 0.55195 | 0.34504 | 0.16788 |
| Si | 0.14661 | 0.07768 | 0.09336 |
| Cu | 0.028778 | 0.019224 | 0.009528 |
| Zn | 0.23050 | 0.21762 | 0.21922 |
| P | 0.69492 | 0.79784 | 0.88909 |
| Fe | 23.087 | 15.281 | 7.395 |
| Pt | 50.142 | 59.594 | 69.575 |
| PRE | 26.58 | 26.58 | 26.58 |
| Density | 11.4 g/cc | 12.3 g/cc | 13.6 g/cc |
| Hardness | 24.3 HRC | 28.7 HRC | 56.8 HRC |
| UTS | 142 ksi | | |
| 0.2% offset yield strength | 81 ksi | | |
| % Elongation | 45 | | |
| Modulus | 31 msi | | |

Table 2 shows the compositions and characterization of the three alloy compositions. Chemical analysis was performed using inductively-coupled plasma (ICP) techniques. Small ingots of the alloys were prepared in a laboratory vacuum arc melting furnace using a thoriated tungsten tip and a triple melt procedure. A homogenization heat treatment cycle was performed on the as-cast ingots at about 1289-1300° C. for about 6 hours (including a ramp up time of about 1 hour). The samples were then cooled to 700° C. in the furnace, and subsequently air cooled. For the 50 percent by weight. Pt sample, a rolled strip was produced by upsetting and cold rolling from each ingot with a finished thickness of about 0.060 inch. The strip was annealed at about 1040° C. for about 20 minutes and air cooled. The 60 percent by weight. Pt sample cracked during initial cold rolling, and the 70 percent by weight. Pt sample cracked during rough machining prior to upset forging. It is believed that the rolling serves to refine the as-cast dendritic or columnar grains into fine, equiaxed grains, and the properties of the alloys are produced by the final heat treatment.

The pitting resistance equivalent (PRE) was calculated as described above.

Density was measured using a Micrometrics gas displacement pycnometer. Pieces of strip were weighed on a balance and then placed in a pycnometer chamber. The volume in the chamber was measured with helium gas and the density of the samples was calculated. The results presented in Table 2 are the average density of three tests on each sample.

Scanning electron microscopy (SEM) analysis revealed no significant platinum segregation.

To reveal the microstructure, the samples were polished and immersion etched in an etchant of 30 mL water, 35 mL HCl, and 5 mL HNO$_3$, heated to 50-70° C. Optical photomicrographs taken at 500× magnification of a longitudinal cross-section of the 50 weight percent Pt sample revealed a microstructure having equiaxed austenite grains with few twin band. Optical photomicrographs taken at 50× magnification of a longitudinal cross-section of the 60 weight percent Pt sample revealed a microstructure having textured, elongated grains. Optical photomicrographs taken at 50× magnification of a longitudinal cross-section of the 70 weight percent Pt sample revealed a microstructure having equiaxed austenite grains with a martensitic structure within the grains.

The hardness of the samples was determined using microhardness testing on the metallographic cross-sections using a 500 gram-force Vickers indentation (ASTM E384). The Vickers hardness was then converted to Rockwell C scale values. As shown in Table 2, the hardness of the samples increased with increasing platinum concentration, with the hardness of the 70 weight percent Pt sample having a hardness similar to that of tool steels. The hardness values shown in Table 2 are an average of five measurements for each sample.

The strength of the samples was determined by tensile testing in accordance with ASTM E8.

In other embodiments, other stainless steels can be combined with one or more element X. The stainless steels can be members of the austenitic stainless steel family, such as the 200 series (e.g., 201 and 202) and the 300 series (e.g., 304L, 302, 308, 309, and 310); the ferritic stainless steel family (e.g., 18-2FM, 405, 409, 429, 430, and 442); and members of the martensitic stainless steel family (such as 403, 410, 416, 420, 440C, 502, 503, and 504).

All of the features disclosed herein may be combined in any combination. Each feature disclosed may be replaced by an alternative feature serving the same, equivalent, or similar purpose. Thus, unless expressly stated otherwise, each feature disclosed is only an example of a generic series of equivalent or similar features.

All publications, applications, and patents referred to in this application are herein incorporated by reference to the same extent as if each individual publication or patent was specifically and individually indicated to be incorporated by reference in their entirety.

Other embodiments are within the claims.

What is claimed is:

1. A medical device, comprising
   an alloy comprising a stainless steel and greater than 50% by weight of one or more first elements selected from the group consisting of palladium, iridium, rhodium, gold, silver, and lead.

2. The device of claim 1, wherein the stainless steel is a 300 series stainless steel.

3. The device of claim 2, wherein the stainless steel is 316 stainless steel.

4. The device of claim 1, wherein the alloy comprises greater than about 60% by weight of the first element.

5. The device of claim 1, wherein the alloy comprises greater than about 70% by weight of the first element.

6. The device of claim 1, wherein the alloy further comprises chromium and molybdenum.

7. The device of claim 1, wherein the alloy is at least about 50% martensitic.

8. The device of claim 1, wherein the alloy consists essentially of the stainless steel, one or more first elements, chromium, and molybdenum.

* * * * *